(12) United States Patent
Lee et al.

(10) Patent No.: US 10,138,188 B2
(45) Date of Patent: Nov. 27, 2018

(54) CATALYST FOR PRODUCING METHANOL PRECURSOR, METHANOL PRECURSOR PRODUCED USING THE CATALYST AND METHANOL PRODUCED USING THE METHANOL PRECURSOR

(71) Applicant: KOREA INSTITUTE OF SCIENCE AND TECHNOLOGY, Seoul (KR)

(72) Inventors: Hyun Joo Lee, Seoul (KR); Hyunah Choo, Seoul (KR); Seungmi Yeo, Seoul (KR); Tran Huyen Dang, Seoul (KR); Jieon Lee, Seoul (KR); Soon Hyeok Hong, Seoul (KR); Dabon Lee, Seoul (KR); Sang Deuk Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/653,970

(22) Filed: Jul. 19, 2017

(65) Prior Publication Data

US 2018/0179130 A1 Jun. 28, 2018

(30) Foreign Application Priority Data

Dec. 27, 2016 (KR) .......................... 10-2016-0179779

(51) Int. Cl.
| | | |
|---|---|---|
| *B01J 27/02* | (2006.01) | |
| *B01J 31/22* | (2006.01) | |
| *C07C 29/12* | (2006.01) | |
| *C07C 29/48* | (2006.01) | |
| *C07C 31/04* | (2006.01) | |
| *C07C 303/24* | (2006.01) | |
| *C07C 305/06* | (2006.01) | |

(52) U.S. Cl.
CPC .............. *C07C 29/48* (2013.01); *B01J 27/02* (2013.01); *B01J 31/226* (2013.01); *C07C 29/12* (2013.01); *C07C 31/04* (2013.01); *B01J 2531/828* (2013.01)

(58) Field of Classification Search
CPC .... B01J 31/0228; B01J 31/12; B01J 31/1616; C07C 29/095; C07C 305/04; C07C 31/04
See application file for complete search history.

(56) References Cited

U.S. PATENT DOCUMENTS

2003/0120125 A1  6/2003  Periana et al.

FOREIGN PATENT DOCUMENTS

| JP | 2001-524125 A | 11/2001 |
| KR | 10-2015-0047993 A | 5/2015 |
| WO | WO 1998/050333 A1 | 11/1998 |

OTHER PUBLICATIONS

Veldman et al., "N1,N1-Dimethyl-3-oxopiperazinium(1+) trichloro(dimethyl sulfoxide-S)platinate(1−), (C6H13N2O)[PtCI3(C2H6OS)]" Acta Crystallographica Section C, vol. 50, Issue 10, pp. 1572-1574, Oct. 1994.*

Bell et al., "A High Yield, Liquid-Phase Approach for the Partial Oxidation of Methane to Methanol uisng SO3 as the Oxidant," Anv. Synth. Catal. 2005, 347, 1203-1206. (Year: 2005).*

Hush et al., "Homogeneous Conversion of Methane to Methanol. 1. Catalytic Activation and Functionalization of Methane by cis-Platin in Sulfuric acid: A Density Functional Study of the Thermochemistry," J. Am. Chem. Soc. 1999, 121, 4633-4639. (Year: 1999).*

Lucio Cattalini et al., "Nucleophilic Displacement of the Chelating Bis (sulfoxide) from cis—[meso-1,2-Bis(phenylsulfinyl) ethane]dichloroplatinum(II) and cis-[rac-1,2-Bis (phenylsulfinyl) ethane] dichloroplatinum(II)", Inorganic Chemistry, 1981, pp. 71-75, vol. 20, No. 1.

William Kitching et al., "Spectroscopic Studies Alkyl Sulfoxide Complexes of Platinum (II) and Palladium (II)", Inorganic Chemistry, Mar. 1970, pp. 541-549, vol. 9, No. 3.

\* cited by examiner

*Primary Examiner* — Pancham Bakshi
*Assistant Examiner* — Mark R Luderer
(74) *Attorney, Agent, or Firm* — Rabin & Berdo, P.C.

(57) ABSTRACT

Disclosed is a novel catalyst for producing a methanol precursor. The use of the catalyst enables the production of a methanol precursor and methanol with high efficiency under low temperature and low pressure conditions. Also disclosed are a methanol precursor produced using the catalyst and methanol produced using the methanol precursor.

4 Claims, 9 Drawing Sheets

CATALYST FOR PRODUCING METHANOL PRECURSOR, METHANOL PRECURSOR PRODUCED USING THE CATALYST AND METHANOL PRODUCED USING THE METHANOL PRECURSOR

CROSS-REFERENCE TO RELATED APPLICATIONS

This application claims, under 35 U.S.C. § 119, the priority of Korean Patent Application No. 10-2016-0179779 filed on Dec. 27, 2016 in the Korean Intellectual Property Office, the disclosure of which is incorporated herein by reference in its entirety.

BACKGROUND OF THE INVENTION

1. Field of the Invention

The present invention relates to a catalyst that can be used to produce a methanol precursor and methanol with high efficiency under low temperature and low pressure conditions, a methanol precursor produced using the catalyst, and methanol produced using the methanol precursor.

2. Description of the Related Art

Petroleum-based oil has been widely used as an energy source around the world but its reserves on the earth is decreasing. In contrast, the reserves of natural gas consisting primarily of methane gas are about 40% larger than those of oil. Furthermore, natural gas is a cheap and abundant energy source that is found all over the world.

However, due to the very low boiling point of methane (−161.5° Q, a major component of natural gas has a very low boiling point (−161.5° Q. It has many restrictions on transportation and storage. Therefore, a large volume of natural gas is re-injected to the underground or burned off. If methane can be converted to C2+ hydrocarbons, methanol, and other petrochemical fuels by partial oxidation, it can provide a solution to overcome the disadvantages of methane gas and enable a larger amount of methane gas to use in various applications.

However, these conversion techniques producing methanol or other hydrocarbon from methane is difficult to control due to the thermochemical stability of methane; bond dissociation energy of C—H in methane is 435 kJ/mol. Therefore, such liquefaction techniques require high temperature (≥700° C.) and high pressure reaction conditions, which resulted to high cost and low yield for those reactions.

Specifically, according to prior art methods, methanol is synthesized from syngas ($CO/H_2$) at a high temperature of 800° C., which requires high equipment cost, and a large quantity of energy.

In an attempt to solve such problems, (bpym)$PtCl_2$, called the Periana catalyst, was developed. However, the turnover number (TON) and turnover frequency (TOF) of the Periana catalyst in the synthesis of methanol from methane gas are limited to 500 and 36/h, respectively.

Techniques for producing methanol by reacting methane gas with oxygen using a heterogeneous catalyst have also been developed. However, the reaction still requires a high temperature of 600° C. or above and the catalyst has a very low selectivity less than 10% despite its high ability to convert methane gas to methanol.

Thus, there is a need to develop a novel catalyst that exhibits good catalytic activity and can be used to produce a methanol precursor in high yield and a method for producing methanol from the methanol precursor in an easy manner.

PRIOR ART DOCUMENTS

Patent Documents

Korean Patent Publication No. 2015-0047993
U.S. Patent Publication No. 2003-0120125

SUMMARY OF THE INVENTION

One object of the present invention is to provide a catalyst that can be used to produce a methanol precursor and methanol with high efficiency under low temperature and low pressure conditions.

A further object of the present invention is to provide a methanol precursor produced using the catalyst.

Another object of the present invention is to provide methanol produced using the methanol precursor.

One aspect of the present invention provides a catalyst for producing a methanol precursor, represented by Formula 1:

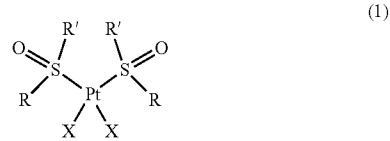

wherein X is selected from the group consisting of Cl, Br, I, and F and R and R' are the same as or different from each other and are each independently selected from the group consisting of a hydrogen atom, substituted or unsubstituted $C_1$-$C_7$ alkyl groups, substituted or unsubstituted $C_8$-$C_{30}$ alkyl groups, substituted or unsubstituted $C_6$-$C_{40}$ aryl groups, and substituted or unsubstituted $C_2$-$C_{30}$ heteroaryl groups; or Formula 2:

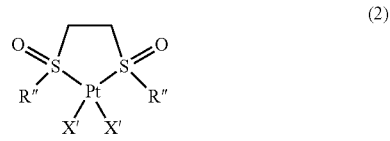

wherein X' is selected from the group consisting of Cl, Br, I, and F and R" is selected from the group consisting of a hydrogen atom, substituted or unsubstituted $C_1$-$C_7$ alkyl groups, substituted or unsubstituted $C_8$-$C_{30}$ alkyl groups, substituted or unsubstituted $C_6$-$C_{40}$ aryl groups, and substituted or unsubstituted $C_2$-$C_{30}$ heteroaryl groups.

R and R' in Formula 1 and R" in Formula 2 may be each independently substituted with one or more atoms or groups selected from the group consisting of a hydrogen atom, a cyano group, halogen atoms, a hydroxyl group, a nitro group, $C_1$-$C_{40}$ alkyl groups, and $C_1$-$C_{40}$ alkoxy groups.

Specifically, the catalyst may be selected from the group consisting of the compounds represented by Formulae 3 to 9:

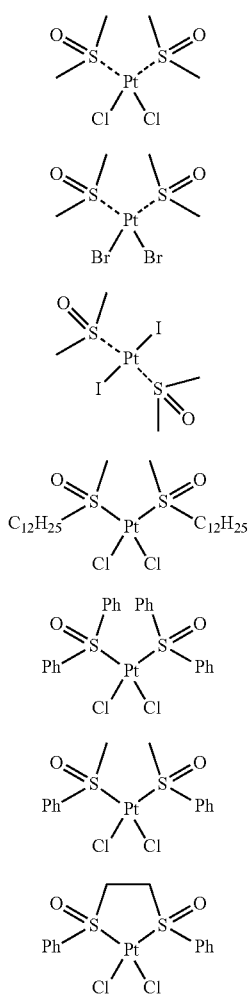

A further aspect of the present invention provides a methanol precursor that is produced by reacting the catalyst with methane gas in an acid solution.

The catalyst may be mixed with the acid solution in a weight ratio of 0.000001-0.1:1.

The methanol precursor may be a methyl ester and the acid solution may be an aqueous sulfuric acid solution or fuming sulfuric acid containing 1 to 60% by weight of $SO_3$.

Another aspect of the present invention provides a functional derivative that is produced by reacting the methanol precursor with a nucleophile.

The nucleophile may be water and the functional derivative may be methanol.

Another aspect of the present invention provides a method for producing a methanol precursor, including (A) mixing the catalyst with an acid solution and supplying methane gas at a pressure of 10 to 50 bar to the mixture.

Step (A) may be carried out at a temperature of 150 to 300° C.

Yet another aspect of the present invention provides a method for producing methanol, including (A) mixing the catalyst with an acid solution and supplying methane gas at a pressure of 10 to 50 bar to the mixture to produce a methanol precursor and (B) reacting the methanol precursor with water to produce methanol.

Step (B) may be carried out at a temperature of 25 to 100° C.

The catalyst of the present invention can induce the progress of the reaction under low temperature and low pressure conditions and is effective in producing a large amount of the methanol precursor due to its good catalytic activity.

In addition, the catalyst of the present invention is simple to prepare, which is advantageous in terms of economic efficiency, and is highly stable so as not to be lost and decomposed during the reaction, ensuring its long-term use.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
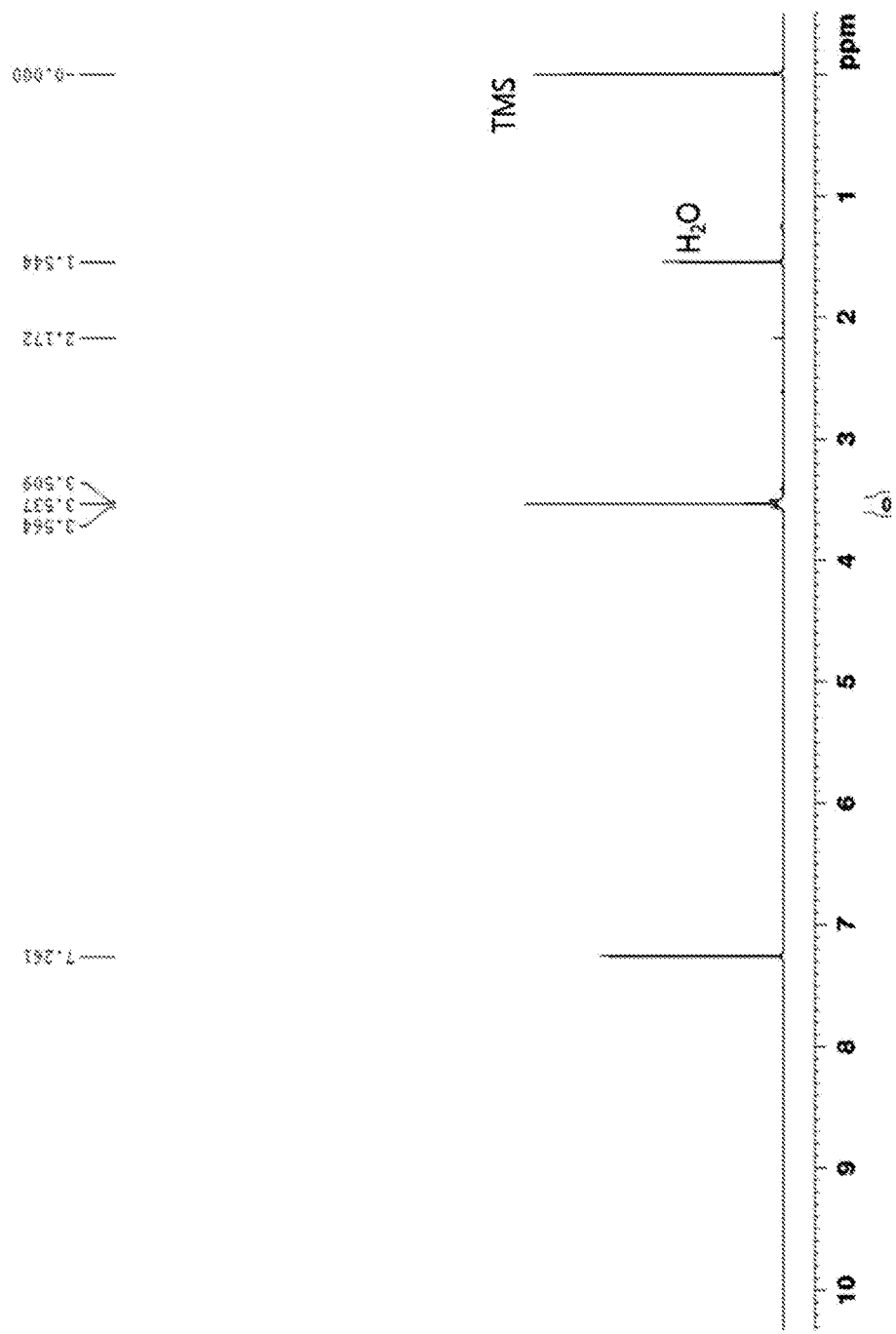
FIG. 1 is a $^1$H-NMR spectrum of the compound represented by Formula 3.

The present invention is directed to a catalyst that can be used to produce a methanol precursor and methanol with high efficiency under low temperature and low pressure conditions, a methanol precursor produced using the catalyst, and methanol produced using the methanol precursor.

The present invention will now be described in detail.

The present invention provides a catalyst for producing a methanol precursor, represented by Formula 1:

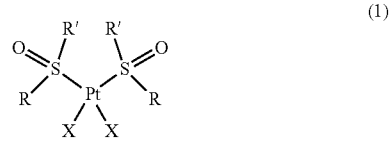

(1)

wherein X is selected from the group consisting of Cl, Br, I, and F and R and R' are the same as or different from each other and are each independently selected from the group consisting of a hydrogen atom, substituted or unsubstituted $C_1$-$C_7$ alkyl groups, substituted or unsubstituted $C_8$-$C_{30}$ alkyl groups, substituted or unsubstituted $C_6$-$C_{40}$ aryl groups, and substituted or unsubstituted $C_2$-$C_{30}$ heteroaryl groups; or Formula 2:

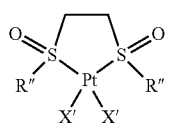
(2)

wherein X' is selected from the group consisting of Cl, Br, I, and F and R" is selected from the group consisting of a hydrogen atom, substituted or unsubstituted $C_1$-$C_7$ alkyl groups, substituted or unsubstituted $C_8$-$C_{30}$ alkyl groups, substituted or unsubstituted $C_6$-$C_{40}$ aryl groups, and substituted or unsubstituted $C_2$-$C_{30}$ heteroaryl groups.

R and R' in Formula 1 and R" in Formula 2 may be each independently substituted with one or more atoms or groups selected from the group consisting of a hydrogen atom, a cyano group, halogen atoms, a hydroxyl group, a nitro group, $C_1$-$C_{40}$ alkyl groups, and $C_1$-$C_{40}$ alkoxy groups.

Specifically, the catalyst is selected from the group consisting of the compounds represented by Formulae 3 to 9:

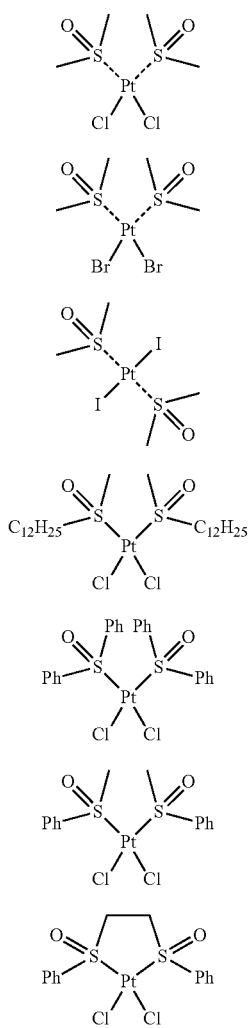

The catalyst of the present invention does not need to be regenerated for reuse and is highly stable enough to maintain its activity even after repeated use.

The present invention also provides a methanol precursor produced using the catalyst.

The methanol precursor of the present invention is produced by reacting the catalyst with methane gas.

Specifically, the methanol precursor of the present invention is produced by a method including (A) mixing the catalyst with an acid solution, supplying methane gas at a pressure of 10 to 50 bar, preferably 25 to 35 bar, to the mixture, and allowing the reaction to proceed at a temperature of 150 to 300° C., preferably 200 to 250° C.

Any acid solution suitable for the production of the methanol precursor may be used without particular limitation. Preferably, the acid solution is an aqueous sulfuric acid solution or fuming sulfuric acid. The fuming sulfuric acid refers to a solution of sulfur trioxide ($SO_3$). The content of $SO_3$ in the fuming sulfuric acid is from 1 to 60% by weight, preferably from 15% to 30% by weight. For example, fuming sulfuric acid containing 20% by weight of $SO_3$ means the presence of 20 g of $SO_3$ in 100 g of fuming sulfuric acid.

The catalyst of the present invention is highly stable so as not to be easily lost, destroyed, and decomposed in such a strongly acidic atmosphere or by oxidation and can be used to produce the methanol precursor through an esterification reaction to oxidize the C—H bond of methane, indicating its good catalytic activity.

The production of the methanol precursor may vary depending on the weight ratio between the catalyst and the acid solution. Accordingly, the weight ratio between the catalyst and the acid is considered a very important factor in producing the methanol precursor in high yield.

The content of the catalyst is adjusted to 0.00001 to 1 mmol or the weight ratio between the catalyst and the acid solution is adjusted to 0.000001-0.1:1, preferably 0.000001-0.001:1, such that a TON of 1000 or above and a TOF of 300/h or above are achieved. If the ratio of the catalyst to the acid solution is <0.000001:1, TON and TOF values may considerably decrease. Meanwhile, if the ratio of the catalyst to the acid solution is >0.1:1, a TON of 1000 or less and a TOF of 300/h or less may be obtained. That is, when the catalyst is mixed with the acid solution in the weight ratio defined above, it has at least 10 times higher TON and TOF (/h) values than those of conventional platinum coordination compounds, indicating its good catalytic performance.

The methanol precursor is produced in the temperature range of 150 to 300° C. preferably 200 to 250° C. Out of this range, the catalyst is less catalytically active for the oxidation of the C—H bond of methane, and as a result, a significantly reduced amount of the methanol precursor is produced with significantly reduced TON (≤1000) and TOF (≤300/h). Particularly, if the temperature exceeds the upper limit defined above, the reaction may proceed rapidly, resulting in poor stability of the product and the formation of a large amount of by-products.

Methane gas is supplied at a pressure of 10 to 50 bar, preferably 25 to 35 bar, for the production of the methanol precursor. If the pressure of the methane gas is less than the lower limit defined above even when the temperature condition is satisfied, the catalyst may be less catalytically active for the oxidation of the C—H bond of methane, and as a result, a significantly reduced amount of the methanol precursor may be produced with significantly reduced TON and TOF (/h) values. Meanwhile, if the pressure of the methane gas exceeds the upper limit defined above, significantly reduced TON and TOF (/h) values may be obtained.

Further, when the methane gas is supplied at a pressure of 25 to 35 bar and the reaction is carried out in the preferred temperature range of 200 to 250° C. in step (A), the methanol precursor can be obtained in high yield with a TON of 3,000 to 15,000 and a TOF of 1,000 to 6,000/h.

The methanol precursor is a methyl ester. For example, when an aqueous sulfuric acid solution or fuming sulfuric acid is used as the acid solution, methyl bisulfate is produced as the methanol precursor.

The present invention also provides a functional derivative produced using the methanol precursor produced in step (A).

The functional derivative of the present invention is produced by reacting the methanol precursor with a nucleophile.

Specifically, the method includes (B) reacting the methanol precursor produced in step (A) with water as a nucleophile at 25 to 100° C. preferably 70 to 100° C. to produce methanol.

Any compound having an unshared pair of electrons in the molecule may be used without particular limitation as the nucleophile. Examples of preferred nucleophiles include water, inorganic acids, organic acids, ammonia, alcohols, and phenols.

A methyl ester as the methanol precursor may react with water as the nucleophile to synthesize methanol as the functional derivative. The methyl ester may also react with a hydrogen halide, such as HCl, HBr or HI, as the nucleophile to synthesize a methyl halide as the functional derivative. The methyl ester may also react with $NH_3$ as the nucleophile to synthesize methylamine. The methyl ester may also react with $H_2S$ as the nucleophile to synthesize methanethiol. The methyl ester may also react with HCN as the nucleophile to synthesize methyl cyanide. Alternatively, the methyl ester may react with trifluoroacetic acid as the nucleophile to synthesize methyl trifluoroacetate.

The functional derivative, preferably methanol, is produced at a temperature of 25 to 100° C. preferably 70 to 100° C. The functional derivative may not be obtained at a temperature less than the lower limit defined above. Meanwhile, further energy is consumed without a significant increase in yield at a temperature exceeding the upper limit defined above.

The series of steps of producing the methanol precursor using the catalyst and producing methanol using the methanol precursor is depicted in Reaction Scheme 1:

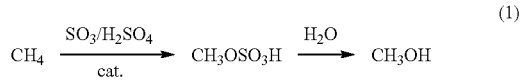

(1)

wherein "cat." represents the catalyst represented by Formula 1 or 2 for producing the methanol precursor.

The use of the catalyst according to the present invention ensures high-yield production of the methanol precursor and methanol under low temperature and low temperature conditions and provides better results in terms of TON and TOF values than the use of conventional platinum catalysts. In addition, since the catalyst of the present invention is highly stable so as not to be damaged, lost, and decomposed during use, it can be used for a long time without loss. Furthermore, due to its good catalytic activity, the use of a small amount of the catalyst leads to the production of a large amount of methanol.

The catalyst of the present invention is advantageous in terms of methyl bisulfate production, catalytic activities, such as TON and TOF values, and economic efficiency over the prior art catalyst (bpym)$PtCl_2$, which is known to induce the synthesis of methanol at a reaction temperature of 180 to 220° C. similar to that defined in the present invention. In addition, the catalyst of the present invention is prepared in a simple manner through a greatly reduced number of processing steps, thus being advantageous from an economic and industrial point of view.

The following examples are provided to assist in further understanding of the invention. However, these examples are intended for illustrative purposes only. It will be evident to those skilled in the art that various modifications and changes can be made without departing from the scope and spirit of the invention and such modifications and changes are encompassed within the scope of the appended claims.

EXAMPLES

Synthesis Examples: Synthesis of Catalysts for Producing Methanol Precursor

Synthesis Example 1: Synthesis of the Compound Represented by Formula 3

$K_2PtCl_4$ (0.5 mmol, 0.2 g) was added to excess DMSO (5 ml) and the mixture was then stirred at 70° C. for 12 h. After completion of the reaction, 10 mL of water was added to the reaction mixture. The resulting precipitate was collected by filtration, washed with water, ethanol, and diethyl ether, and dried under vacuum, giving the compound represented by Formula 3. Yield 75%; $^1$H NMR (300 MHz, $CDCl_3$) δ=3.56 (s, 6H) (FIG. 1).

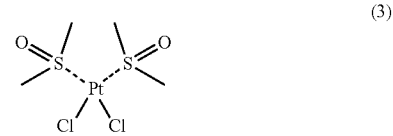

(3)

Synthesis Example 2: Synthesis of the Compound Represented by Formula 4

Figure 2:
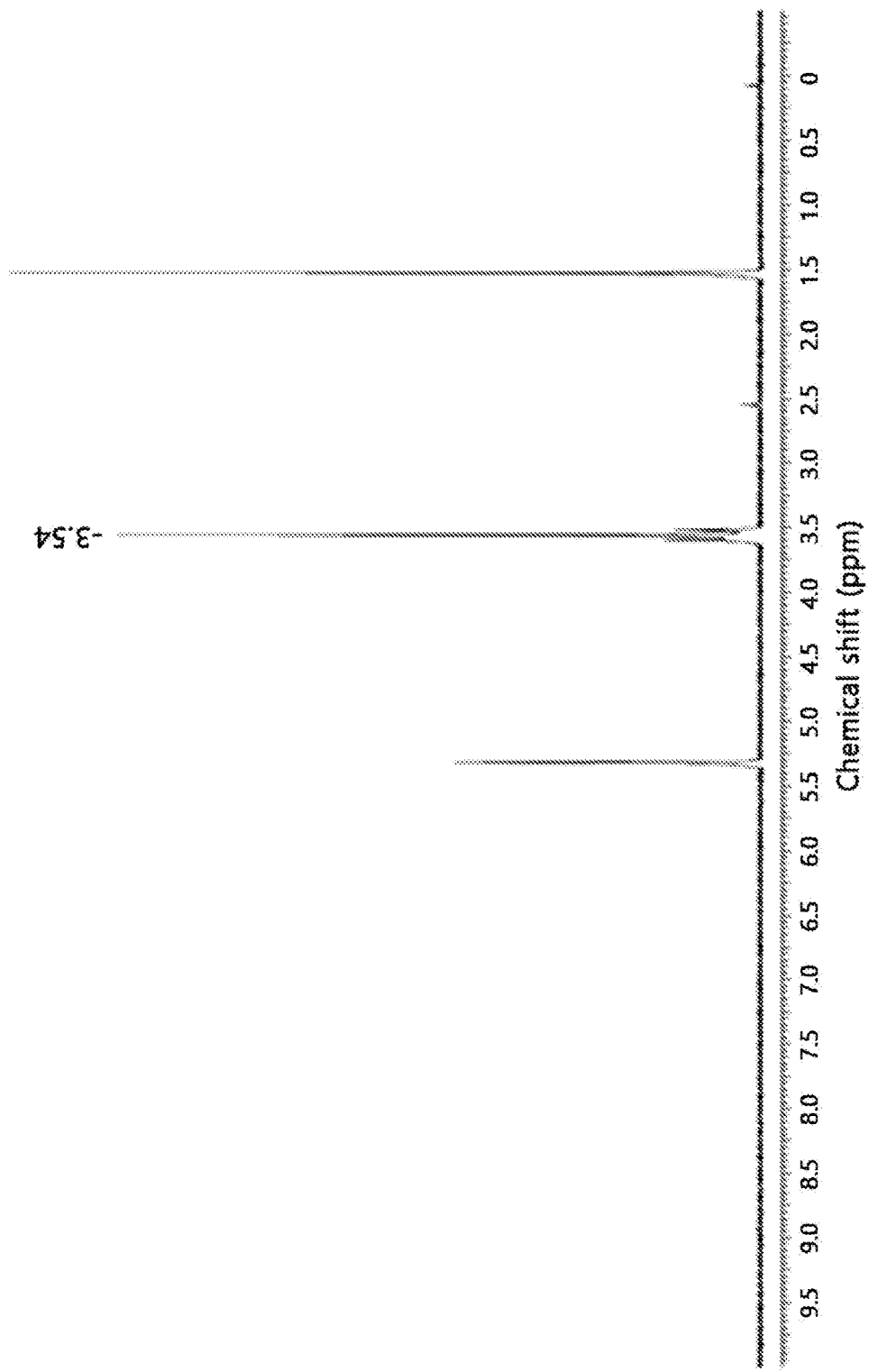
FIG. 2 is a $^1$H-NMR spectrum of the compound represented by Formula 4.

$PtBr_2$ (0.5 mmol, 127 mg) was added to excess DMSO (5 ml) and the mixture was then stirred at 70° C. for 12 h. After completion of the reaction, 10 mL of water was added to the reaction mixture. The resulting precipitate was collected by filtration, washed with water, ethanol, and diethyl ether, and dried under vacuum, giving the compound represented by Formula 4. Yield 61%; $^1$H NMR (300 MHz, $CD_2Cl_2$) δ=3.56 (s, 6H) (FIG. 2).

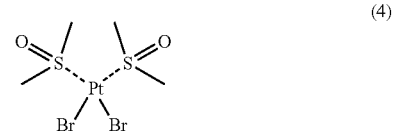

(4)

Synthesis Example 3: Synthesis of the Compound Represented by Formula 5

Figure 3:
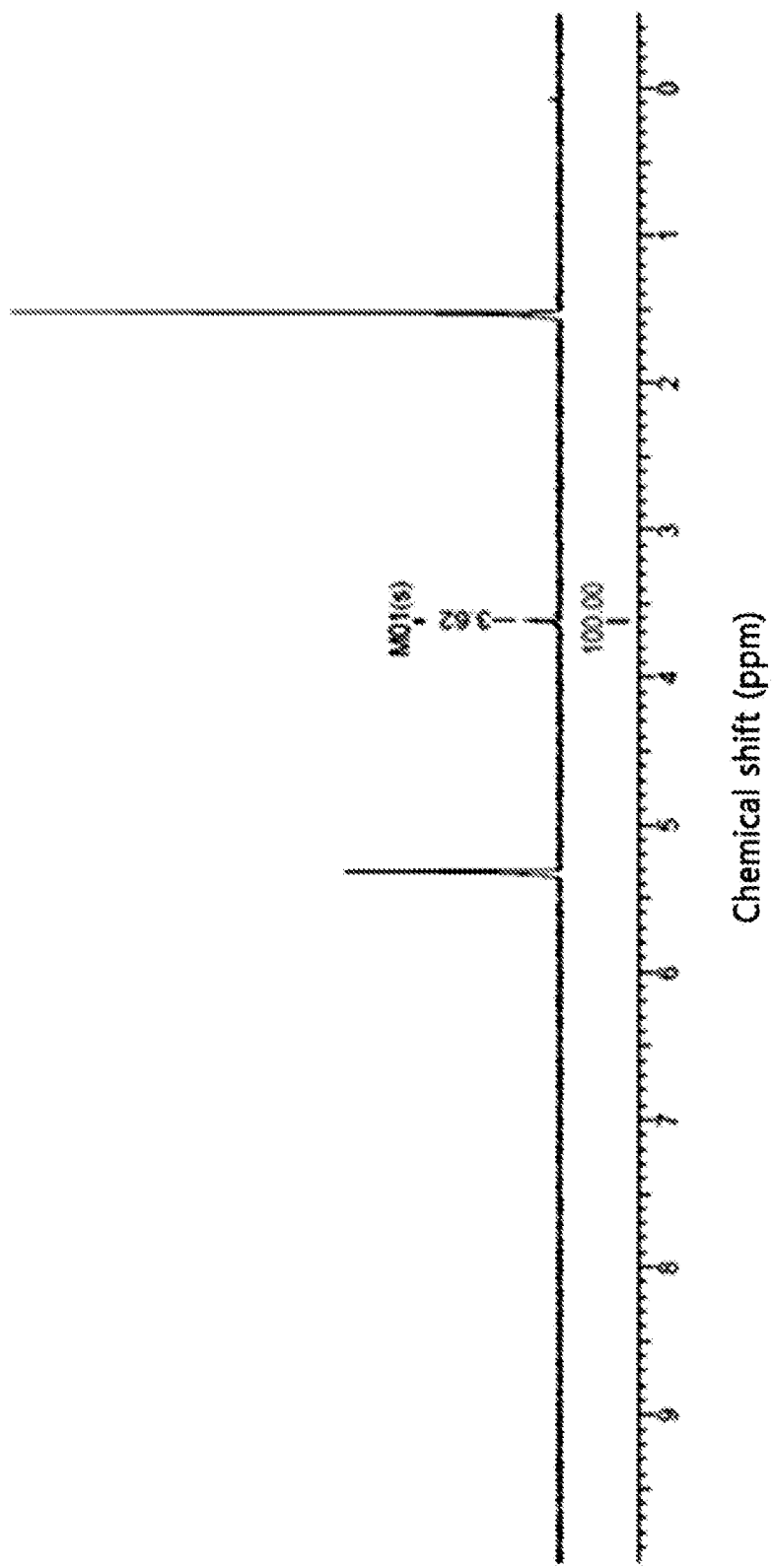
FIG. 3 is a $^1$H-NMR spectrum of the compound represented by Formula 5.

PtI$_2$ (0.5 mmol, 224 mg) was added to excess DMSO (5 ml) and the mixture was then stirred at 70° C. for 12 h. After completion of the reaction, 10 mL of water was added to the reaction mixture. The resulting precipitate was collected by filtration, washed with water, ethanol, and diethyl ether, and dried under vacuum, giving the compound represented by Formula 5. Yield 62%; $^1$H NMR (300 MHz, CD$_2$Cl$_2$) δ=3.62 (s, 6H) (FIG. 3).

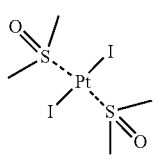

(5)

Synthesis Example 4: Synthesis of the Compound Represented by Formula 6

Figure 4:
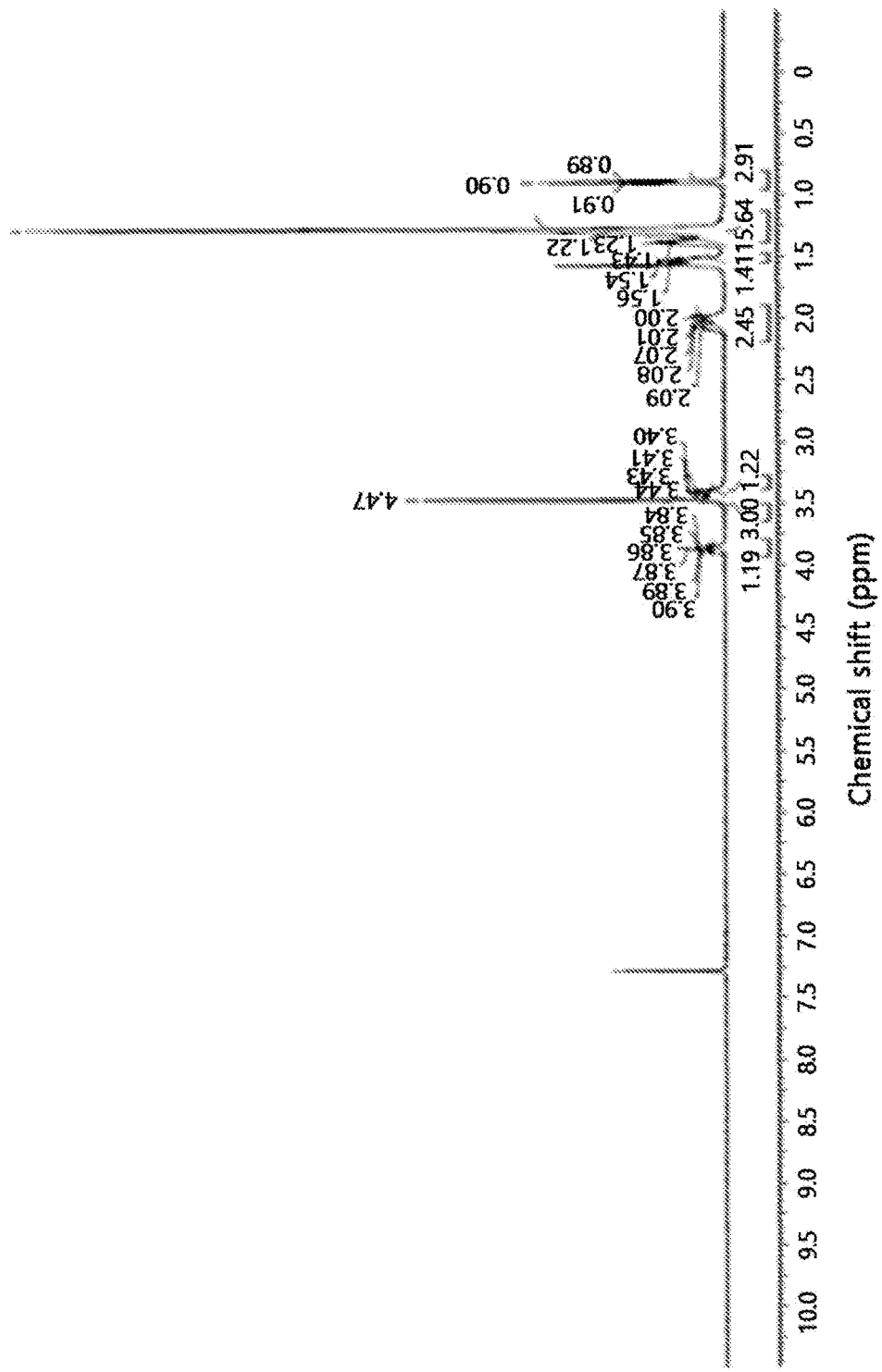
FIG. 4 is a $^1$H-NMR spectrum of the compound represented by Formula 6.

Methyl dodecyl sulfoxide (0.9 mmol, 209 mg) was added to an aqueous solution of K$_2$PtCl$_4$ (0.3 mmol, 125 mg). The mixture was then stirred at room temperature for 12 h. The resulting white precipitate was collected by filtration, washed with water, ethanol, and diethyl ether, and dried under vacuum, giving the compound represented by Formula 6. Yield 43%, $^1$H NMR (500 MHz, CDCl$_3$) δ=3.87 (dt, J=4.6, 12.3 Hz, 1H), 3.47 (s, 3H), 3.41 (dt, J=4.9, 12.2 Hz, 1H), 2.14-1.92 (m, 2H), 1.55-1.48 (m, 2H), 1.43-1.34 (m, 2H), 1.34-1.16 (m, 14H), 0.90 (t, J=6.6 Hz, 3H) (FIG. 4).

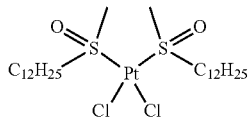

(6)

Synthesis Example 5: Synthesis of the Compound Represented by Formula 7

Figure 5:
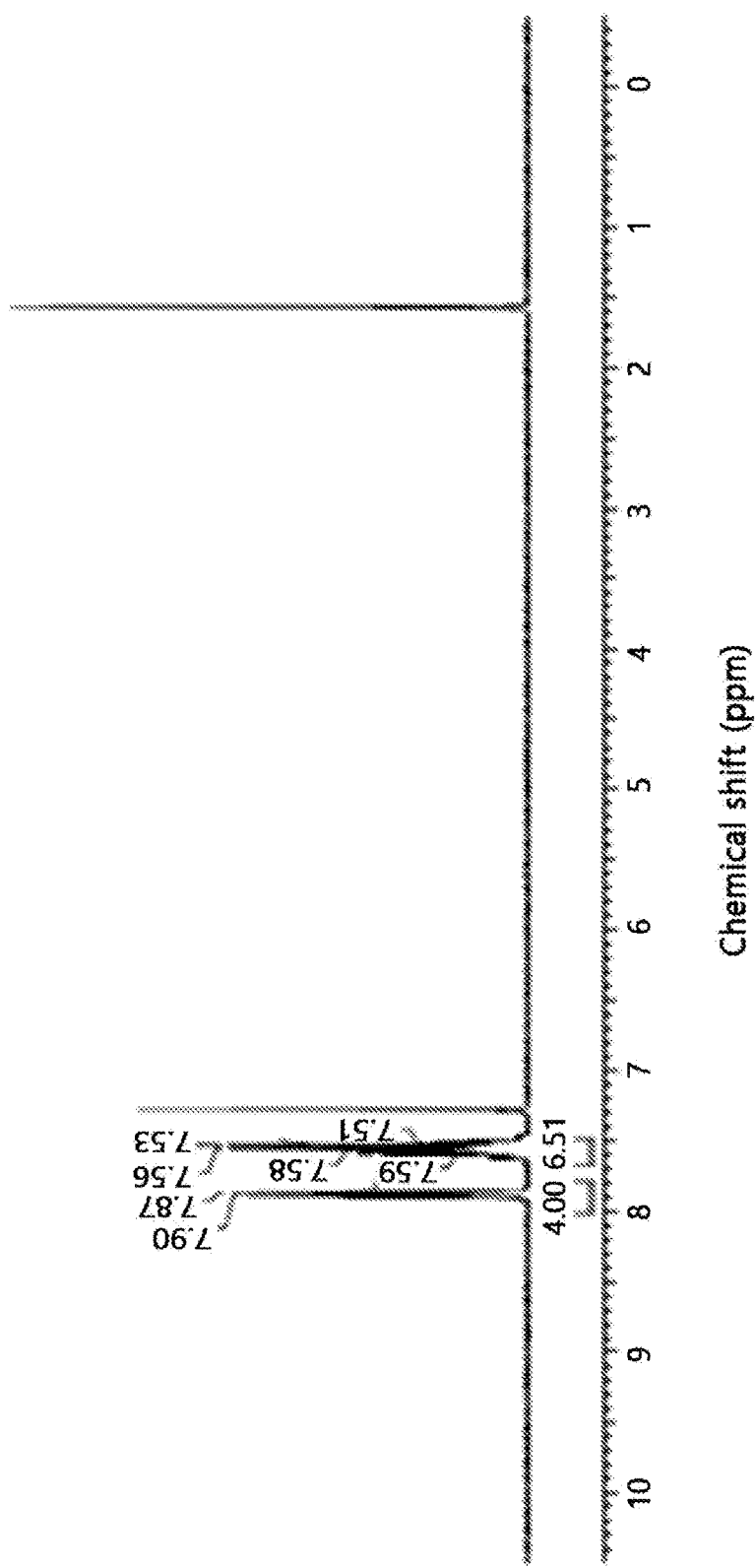
FIG. 5 is a $^1$H-NMR spectrum of the compound represented by Formula 7.

A solution of diphenyl sulfoxide (1.75 mmol, 354 mg) in methanol was mixed with an aqueous solution of K$_2$PtCl$_4$ (0.5 mmol, 208 mg). The mixture was then stirred at room temperature for 12 h. The resulting precipitate was collected by filtration, washed with water, ethanol, and diethyl ether, and dried under vacuum, giving the compound represented by Formula 7. Yield: 33%, $^1$H NMR (300 MHz, CDCl$_3$) δ=7.88 (d, J=7.5 Hz, 4H), 7.64-7.49 (m, 6H) (FIG. 5).

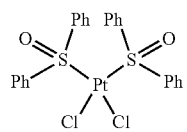

(7)

Synthesis Example 6: Synthesis of the Compound Represented by Formula 8

Figure 6:
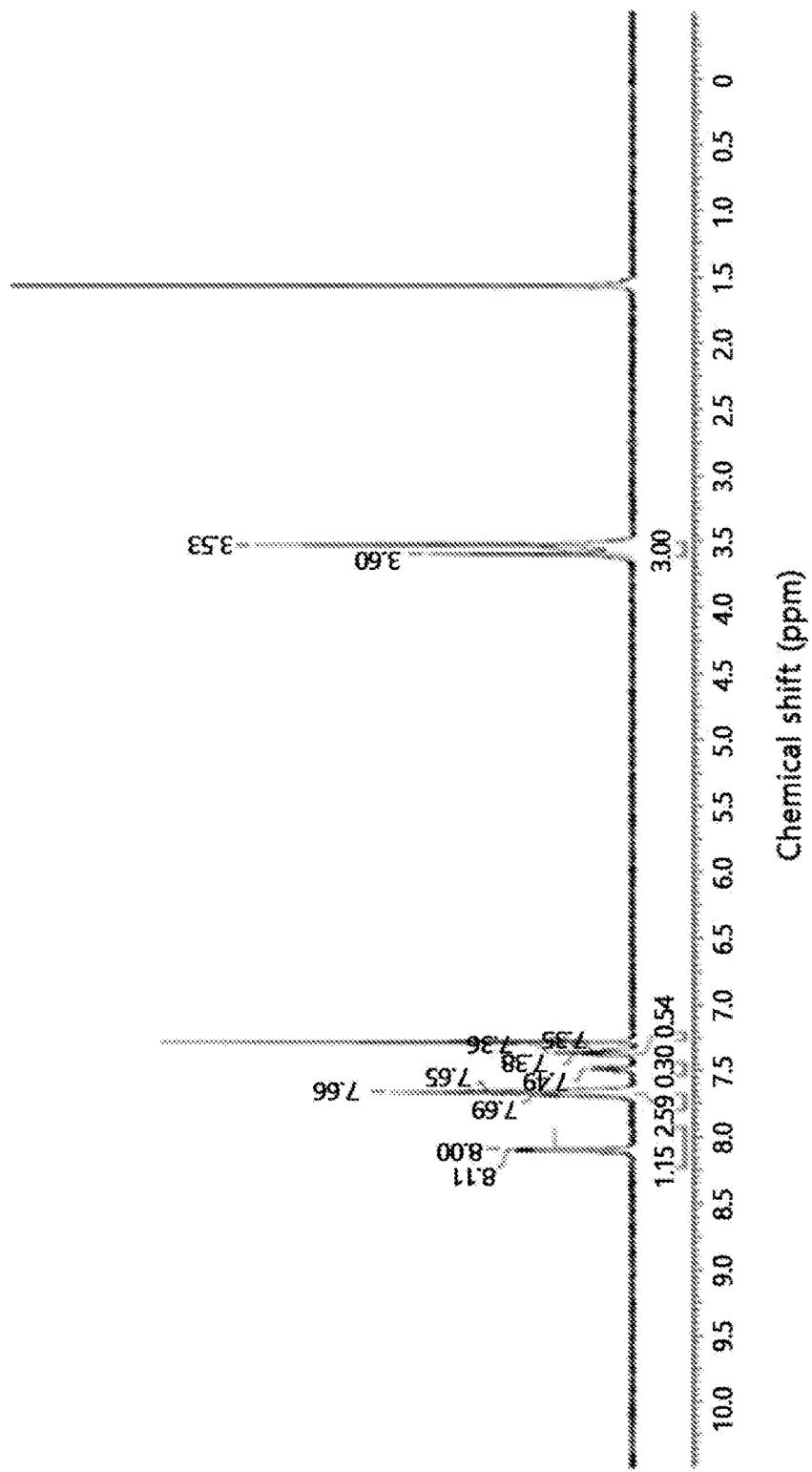
FIG. 6 is a $^1$H-NMR spectrum of the compound represented by Formula 8.

Methyl phenyl sulfoxide (1.5 mmol, 210 mg) was added to an aqueous solution of K$_2$PtCl$_4$ (0.5 mmol, 208 mg). The mixture was then stirred at room temperature for 12 h, giving the compound represented by Formula 8. Yield: 67%, $^1$H NMR (500 MHz, CDCl$_3$) δ=8.15-7.34 (m, 5H), 3.60-3.53 (d, 3H) (FIG. 6).

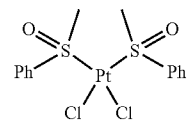

(8)

Synthesis Example 7: Synthesis of the Compound Represented by Formula 9

Figure 7:
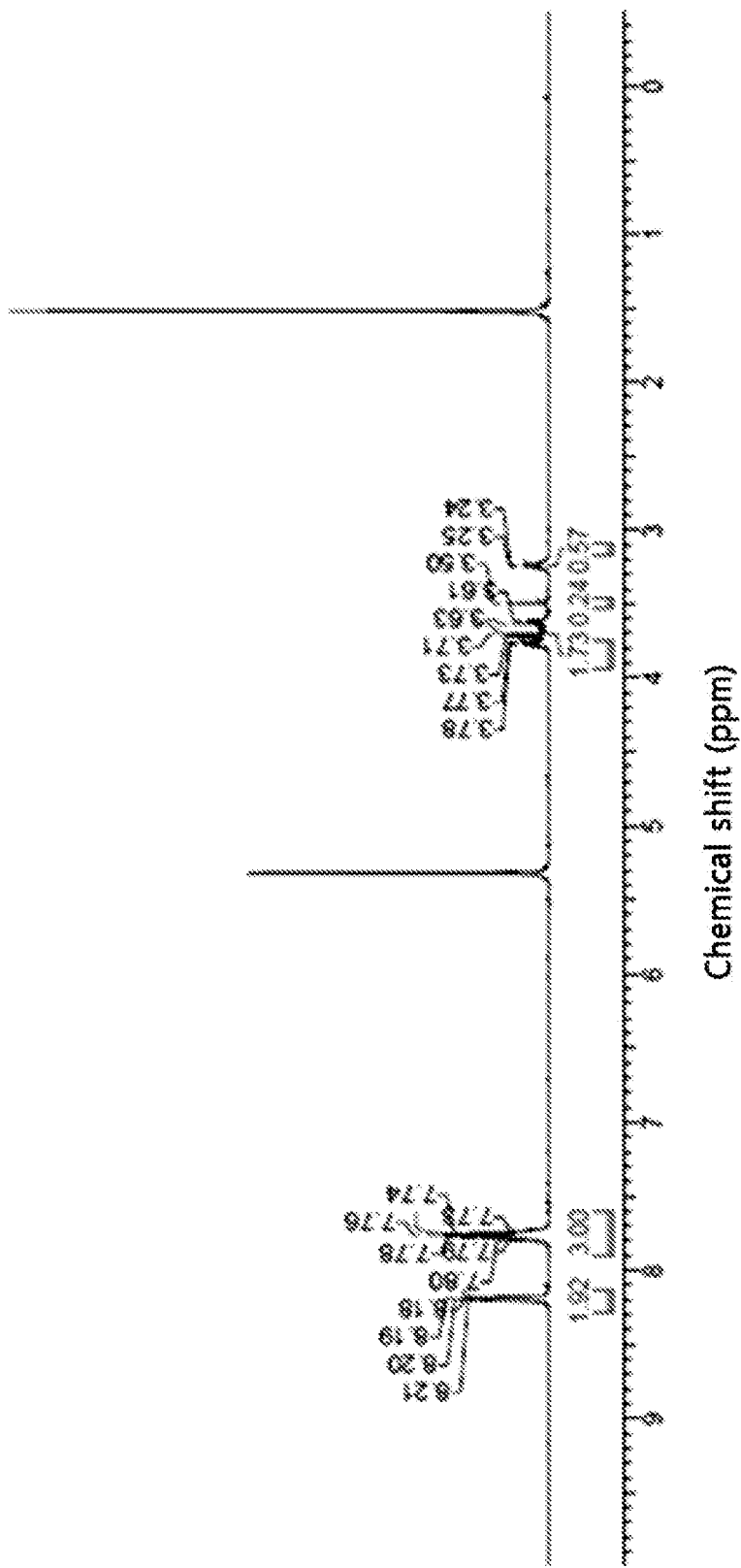
FIG. 7 is a $^1$H-NMR spectrum of the compound represented by Formula 9.

1,2-Bis(phenylsulfinyl)ethane (0.5 mmol, 139 mg) was added to an aqueous solution of K$_2$PtCl$_4$ (0.5 mmol, 208 mg). The mixture was stirred at room temperature for 12 h, giving the compound represented by Formula 9. Yield 26%; $^1$H NMR (500 MHz, CD$_2$Cl$_2$) δ=8.19 (dd, J=4.4, 6.8 Hz, 2H), 7.85-7.62 (m, 3H), 3.80-3.16 (m, 3H) (FIG. 7).

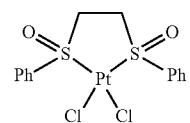

(9)

<Comparison of the Amounts of Methanol Precursor and Methanol Produced when the Catalysts were Used in Different Amounts>

Example 1: Production of Methanol Precursor and Methanol

Figure 8:
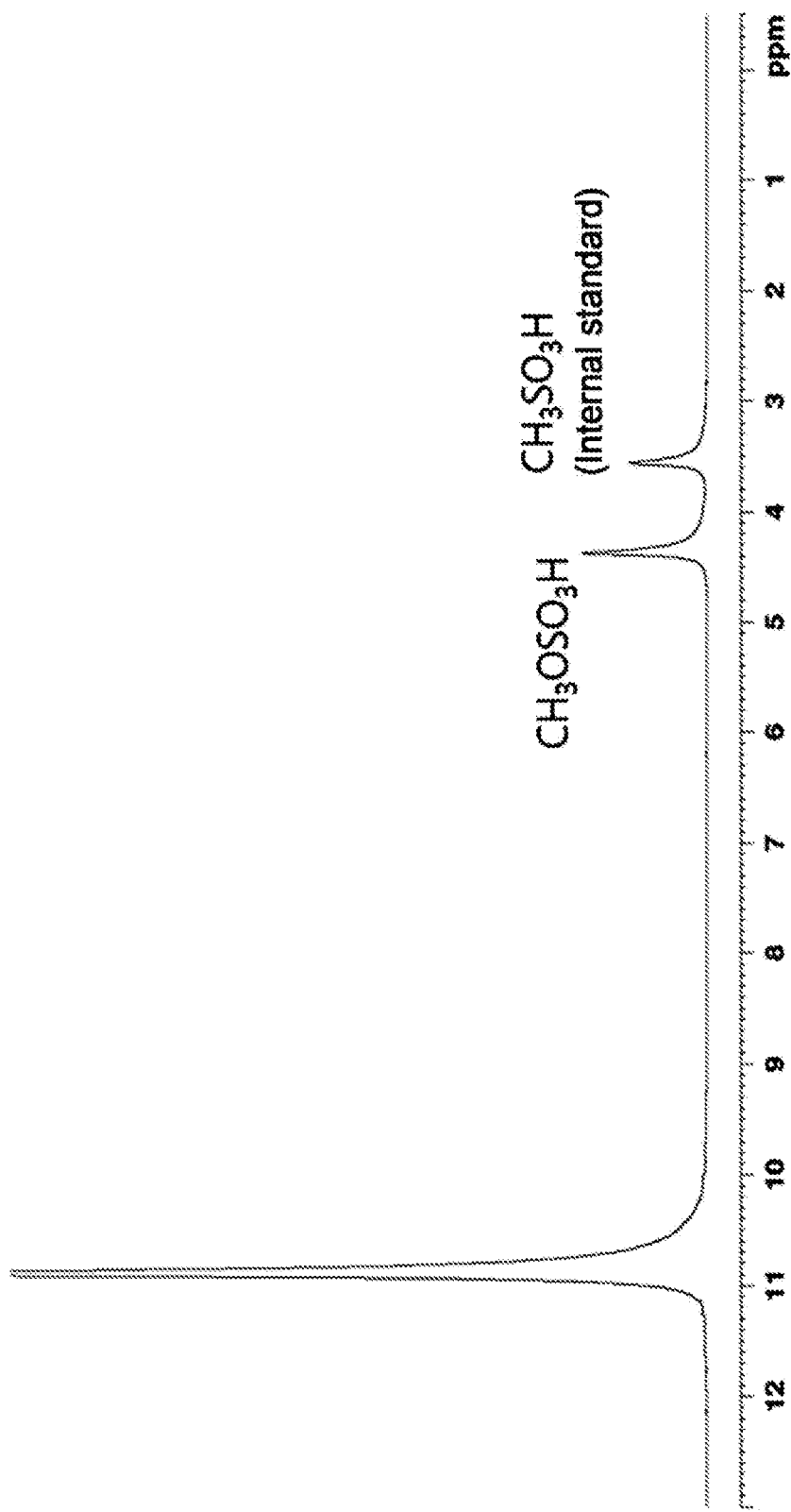
FIG. 8 is a $^1$H-NMR spectrum of methyl bisulfate ($CH_3OSO_3H$) produced in Example 1.

Production of Methyl Bisulfate 5 mg (1.2×10$^{-2}$ mmol) of the catalyst (Formula 3) prepared in Synthesis Example 1 was mixed with 30 g of fuming sulfuric acid containing 20 wt % of SO$_3$ in a 100 ml Inconel autoclave with a glass liner. Methane gas was filled in the reactor until a pressure of 20 bar was reached. The methane-filled reactor was heated to 180° C. and the reaction was allowed to proceed for 3 h. The pressure of the methane at 180° C. was 35 bar at the initial stage of the reaction and decreased to 30 bar after the reaction for 3 h. After completion of the reaction, the components of the reaction mixture were analyzed by $^1$H-NMR spectroscopy using D$_2$SO$_4$ containing methanesulfonic acid (CH$_3$SO$_3$H) as the internal standard (FIG. 8).

FIG. 1 confirms the production of 2.51 g (22.36 mmol) of methyl bisulfate. The turnover number (TON) and turnover frequency (TOF) of the catalyst for the production of methyl bisulfate were calculated to be 1,864 and 621/h, respectively.

Methanol Production 200 g of distilled water was added to the reaction mixture including 2.51 g of methyl bisulfate, and then ethanol as the internal standard was added thereto. The reaction was allowed to proceed at 90° C. for 4 h. After completion of the reaction, the components of the reaction mixture were analyzed by HPLC (FIG. 9).

Figure 9:
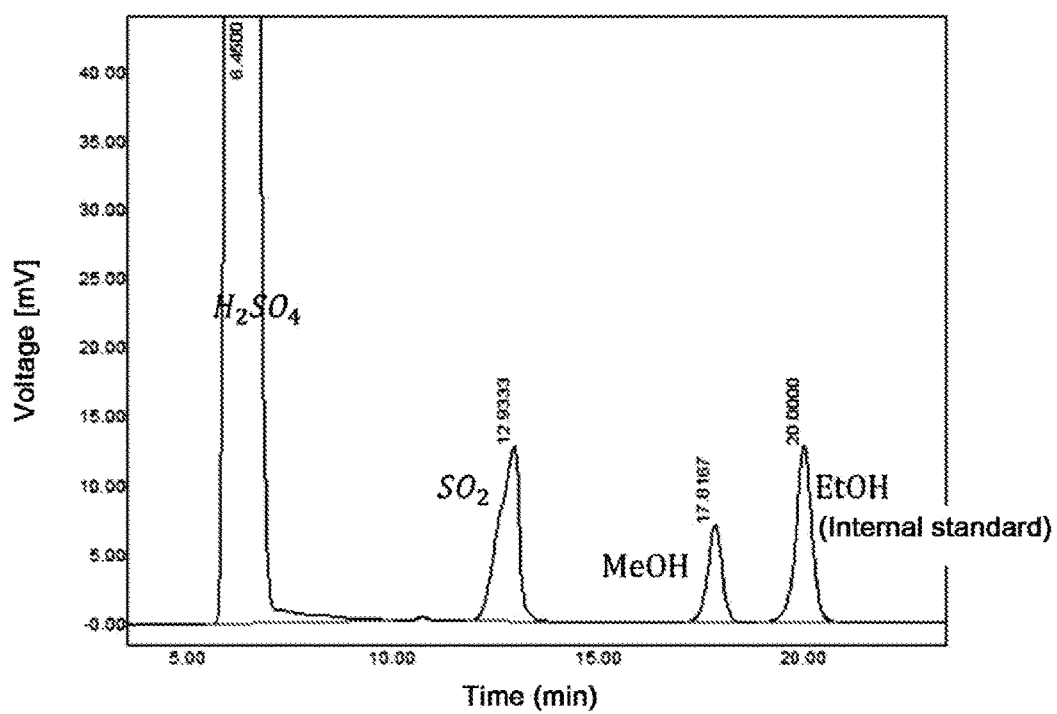
FIG. 9 shows the results of HPLC analysis for methanol produced in Example 1.

FIG. 9 reveals the production of 0.67 g (21.24 mmol) of methanol.

Examples 2-6

Methyl bisulfate and methanol were produced in the same manner as in Example 1, except that the catalyst represented by Formula 3 was used in the amounts shown in Table 1.

Test Example 1

Test Example 1: Amounts of Methyl Bisulfate ($CH_3OSO_3H$) Produced and Measurement of TON and TOF Values TON and TOF values were quantified by $^1$H-NMR spectroscopy.

TABLE 1

| Example No. | Amount of catalyst used | Catalyst:acid solution weight ratio | Amount of methyl bisulfate produced | TON | TOF (/h) |
|---|---|---|---|---|---|
| Example 1 | 5 mg ($1.2 \times 10^{-2}$ mmol) | 0.0016:1 | 2.51 g (22.36 mmol) | 1,864 | 621 |
| Example 2 | 0.1 mg ($2.4 \times 10^{-4}$ mmol) | 0.00003:1 | 0.51 g (4.59 mmol) | 19,125 | 6,375 |
| Example 3 | 0.25 mg ($6 \times 10^{-4}$ mmol) | 0.00008:1 | 0.83 g (7.41 mmol) | 12,350 | 4,116 |
| Example 4 | 0.5 mg ($1.2 \times 10^{-3}$ mmol) | 0.00016:1 | 1.06 g (9.47 mmol) | 7,891 | 2,630 |
| Example 5 | 1 mg ($2.4 \times 10^{-3}$ mmol) | 0.00032:1 | 1.38 g (12.3 mmol) | 5,125 | 1,708 |
| Example 6 | 10 mg ($2.4 \times 10^{-2}$ mmol) | 0.003:1 | 3.16 g (28.2 mmol) | 1,175 | 392 |

As can be seen from the results in Table 1, the TON and TOF of the catalyst for the production of methyl bisulfate increased with decreasing amount of the catalyst. That is, the weight ratio of the catalyst to the acid solution has an important influence on the production of methyl bisulfate and the TON and TOF values of the catalyst.

Particularly, the TON and TOF values of the catalyst in Example 2 were much higher than those in the other examples.

When the catalyst represented by Formula 7 was mixed with the acid solution in a weight ratio of 0.000008-0.0001:1, ≥1 g (8 mmol) of methyl bisulfate was produced with a TON of ≥2000 and a TOF of ≥700/h. Particularly, when $5 \times 10^{-4}$ to $1 \times 10^{-3}$ mmol of the catalyst represented by Formula 7 was used, the largest amount of methyl bisulfate or methanol was produced, demonstrating that even a very small amount of the catalyst is sufficient to convert a large amount of methane gas to methanol.

That is, the catalyst enables the mass production of methyl bisulfate and methanol even when used in a small amount.

<Comparison of the Amounts of Methyl Bisulfate Produced when Different Kinds of Catalysts were Used>

Examples 7-12

Methyl bisulfate and methanol were produced in the same manner as in Example 1, except that the catalysts represented by Formulae 4-9 were used instead of the catalyst represented by Formula 3.

Test Example 2

Test Example 2: Amounts of Methyl Bisulfate ($CH_3OSO_3H$) Produced and Measurement of TON and TOF Values TON and TOF values were quantified by $^1$H-NMR spectroscopy.

TABLE 2

| Example No. | Catalyst | Amount of methyl bisulfate produced | TON | TOF (/h) |
|---|---|---|---|---|
| Example 7 | Formula 4 | 1.11 g (9.90 mmol) | 825 | 275 |
| Example 8 | Formula 5 | 2.86 g (25.34 mmol) | 2,128 | 709 |
| Example 9 | Formula 6 | 2.39 g (21.3 mmol) | 1,775 | 592 |
| Example 10 | Formula 7 | 1.19 g (10.64 mmol) | 887 | 296 |
| Example 11 | Formula 8 | 1.77 g (15.78 mmol) | 1,314 | 438 |
| Example 12 | Formula 9 | 1.64 g (14.63 mmol) | 1,219 | 406 |

The results in Table 2 show that methyl bisulfate was produced in high yields (≥1 g) and the TON and TOF values of the catalysts were high in Examples 7-12.

<Comparison of the Amounts of Methyl Bisulfate Produced Depending on Reaction Conditions>

Examples 13-17

Methyl bisulfate and methanol were produced in the same manner as in Example 1, except that the reaction conditions were changed as shown in Table 3. The amount of the catalyst used was $1.2 \times 10^{-2}$ mmol.

Comparative Examples 1-3

The Periana catalyst (($bpym$)$PtCl_2$) as a conventional platinum catalyst was used for methanol synthesis. Specifically, methyl bisulfate and methanol were produced using different amounts of the Periana catalyst, as shown in Table 3. The Periana catalyst was prepared in a 100 ml Inconel autoclave with a glass liner in accordance with the method described in Solid Catalysts for the Selective Low-Temperature Oxidation of Methane to Methanol, Author: Regina Palkovits Dr., Markus Antonietti Prof. Dr., Pierre Kuhn Dr., Arne Thomas Dr., Ferdi Schrüth Prof. Dr., Volume 48, Issue 37 Sep. 1, 2009 Pages 6909-6912. The results are shown in Table 3.

Test Example 3

Test Example 3: Amounts of Methyl Bisulfate ($CH_3OSO_3H$) Produced and Measurement of TON and TOF Values TON and TOF values were quantified by $^1$H-NMR spectroscopy.

TABLE 3

| Example No. | Amount of catalyst used | Reaction conditions for the synthesis of methyl bisulfate | | Amount of methyl bisulfate produced | TON | TOF (/h) |
| --- | --- | --- | --- | --- | --- | --- |
| | | Temperature (° C.) | Methane gas pressure (bar) | | | |
| Example 1 | Formula 3 $1.2 \times 10^{-2}$ mmol | 180 | 35 | 2.51 g (22.36 mmol) | 1,864 | 621 |
| Example 13 | Formula 3 $1.2 \times 10^{-2}$ mmol | 120 | 35 | 0.12 g (10.7 mmol) | 445 | 148 |
| Example 14 | Formula 3 $1.2 \times 10^{-2}$ mmol | 150 | 35 | 0.42 g (3.75 mmol) | 1,562 | 520 |
| Example 15 | Formula 3 $1.2 \times 10^{-2}$ mmol | 180 | 25 | 1.21 g (9.12 mmol) | 3,800 | 1,266 |
| Example 16 | Formula 3 $1.2 \times 10^{-2}$ mmol | 180 | 10 | 0.70 g (6.26 mmol) | 2,612 | 871 |
| Example 17 | Formula 3 $1.2 \times 10^{-2}$ mmol | 220 | 35 | 3.16 g (28.3 mmol) | 11,791 | 3,930 |
| Comparative Example 1 | 20 mg ($4.7 \times 10^{-2}$ mmol) | 150 | 35 | 0.58 g (5.17 mmol) | 110 | 36 |
| Comparative Example 2 | 5 mg ($1.1 \times 10^{-2}$ mmol) | 180 | 35 | 0.49 g (4.3 mmol) | 366 | 122 |
| Comparative Example 3 | 1 mg ($2.35 \times 10^{-3}$ mmol) | 180 | 35 | — | — | — |

As can be seen from the results in Table 3, methyl bisulfate was produced in higher yields with higher TON and TOF values in Examples 1 and 13-17 than in Comparative Examples 1-3. Particularly, the TON and TOF values of the catalyst used in Comparative Example 2 were much lower than those of the catalyst used in Examples 1 and 13-17 although the amounts of the two catalysts were similar.

When the temperature was lower than or equal to 150° C. (Examples 13 and 14) or the pressure was as low as 10 bar (Example 16), the amount of methyl bisulfate produced was reduced to 1 g or less. Particularly, the TON and TOF values of the catalyst for the production of methyl bisulfate at a temperature of 120° C. in Example 13 were significantly low compared to those in the other examples.

What is claimed is:

1. A method for producing a methanol precursor, comprising (A) mixing a catalyst with an acid solution and supplying methane gas at a pressure of 10 to 50 bar to the mixture, the catalyst being represented by Formula 1:

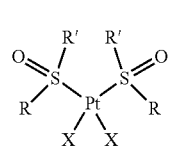

(1)

wherein X is selected from the group consisting of Cl, Br, I and F, and R and R' are the same as or different from each other and are each independently selected from the group consisting of a hydrogen atom, substituted or unsubstituted $C_1$-$C_7$ alkyl groups, substituted or unsubstituted $C_8$-$C_{30}$ alkyl groups, substituted or unsubstituted $C_6$-$C_{40}$ aryl groups, and substituted or unsubstituted $C_2$-$C_{30}$ heteroaryl groups; or Formula 2:

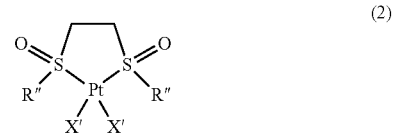

(2)

wherein X' is selected from the group consisting of Cl, Br, I and F, and R" is selected from the group consisting of a hydrogen atom, substituted or unsubstituted $C_1$-$C_7$ alkyl groups, substituted or unsubstituted $C_8$-$C_{30}$ alkyl groups, substituted or unsubstituted $C_6$-$C_{40}$ aryl groups, and substituted or unsubstituted $C_2$-$C_{30}$ heteroaryl groups.

2. The method according to claim 1, wherein step (A) is carried out at a temperature of 150 to 300° C.

3. A method for producing methanol, comprising (A) mixing a catalyst with an acid solution and supplying methane gas at a pressure of 10 to 50 bar to the mixture to produce a methanol precursor and (B) reacting the methanol precursor with water to produce methanol, the catalyst being represented by Formula 1:

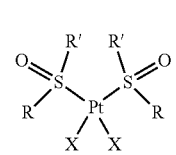

(1)

wherein X is selected from the group consisting of Cl, Br, I and F, and R and R' are the same as or different from each other and are each independently selected from the group consisting of a hydrogen atom, substituted or unsubstituted $C_1$-$C_7$ alkyl groups, substituted or unsubstituted $C_8$-$C_{30}$ alkyl groups, substituted or unsubstituted $C_6$-$C_{40}$ aryl groups, and substituted or unsubstituted $C_2$-$C_{30}$ heteroaryl groups; or Formula 2:

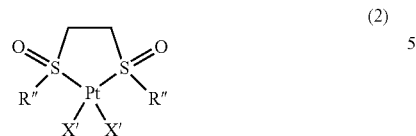

(2)

wherein X' is selected from the group consisting of Cl, Br, I and F, and R" is selected from the group consisting of a hydrogen atom, substituted or unsubstituted $C_1$-$C_7$ alkyl groups, substituted or unsubstituted $C_8$-$C_{30}$ alkyl groups, substituted or unsubstituted $C_6$-$C_{40}$ aryl groups, and substituted or unsubstituted $C_2$-$C_{30}$ heteroaryl groups.

4. The method according to claim 3, wherein step (B) is carried out at a temperature of 25 to 100° C.

* * * * *